(12) United States Patent
Irani

(10) Patent No.: US 6,898,963 B2
(45) Date of Patent: May 31, 2005

(54) APPARATUS AND METHOD FOR MEASURING VISCOSITY

(75) Inventor: Cyrus A. Irani, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 34 days.

(21) Appl. No.: 10/692,877

(22) Filed: Oct. 24, 2003

(65) Prior Publication Data

US 2005/0087001 A1 Apr. 28, 2005

(51) Int. Cl.$^7$ .............................................. G01N 11/04
(52) U.S. Cl. ................................................. 73/54.04
(58) Field of Search ............................. 73/54.04–54.09

(56) References Cited

U.S. PATENT DOCUMENTS

| | | | | |
|---|---|---|---|---|
| 2,988,869 A | * | 6/1961 | Kocher et al. ............... | 368/208 |
| 4,274,279 A | | 6/1981 | Meister | |
| 4,403,502 A | * | 9/1983 | Lindt ........................ | 73/54.09 |
| 4,426,878 A | | 1/1984 | Price et al. | |
| 4,455,860 A | * | 6/1984 | Cullick et al. .............. | 73/19.11 |
| 4,539,837 A | | 9/1985 | Barnaby | |
| 4,566,314 A | * | 1/1986 | Thurston .................... | 73/54.09 |
| 4,574,622 A | * | 3/1986 | Hatfield ..................... | 73/54.04 |
| 4,592,226 A | | 6/1986 | Weber et al. | |
| 6,309,550 B1 | * | 10/2001 | Iversen et al. .............. | 210/644 |

FOREIGN PATENT DOCUMENTS

| | | | | |
|---|---|---|---|---|
| DE | 2452442 A | * | 5/1976 | ........... G01N/11/04 |
| GB | 2 244 338 A | | 11/1991 | |

OTHER PUBLICATIONS

Van Wazer et al., "Viscosity and Flow Measurement," Wiley Interscience, pp. 237–244.*

"Drilling Waste Slurries: Engineering their Properties for Waste Management Solutions"; J.M. Davison et al.; Copyright 2001 AADE National Drilling Technical Conference; Mar. 27–29, 2001; pp. 1–9.

* cited by examiner

Primary Examiner—Hezron Williams
Assistant Examiner—John Fitzgerald
(74) Attorney, Agent, or Firm—Lawrence R. Youst

(57) ABSTRACT

An apparatus and method for measuring the viscosity of a sample fluid are disclosed. In one embodiment, a holding vessel (82) receives the sample fluid (94) and a weighted fluid (96). The weighted fluid (96) has a greater specific gravity than the sample fluid (94). A floating spacer (100) is buoyantly disposed in the weighted fluid (96) such that an interface (116) between the sample fluid (94) and the weighted fluid (96) is defined between the holding vessel (82) and the floating spacer (100). A capillary tube 86 is positioned in fluid communication with the holding vessel (82) such that a pressure drop is created across the capillary tube (86) when at least a portion of the sample fluid (94) is forced therethrough. The viscosity of the sample fluid (94) may be determined by utilizing Hagen–Poiseuille's Law.

36 Claims, 3 Drawing Sheets

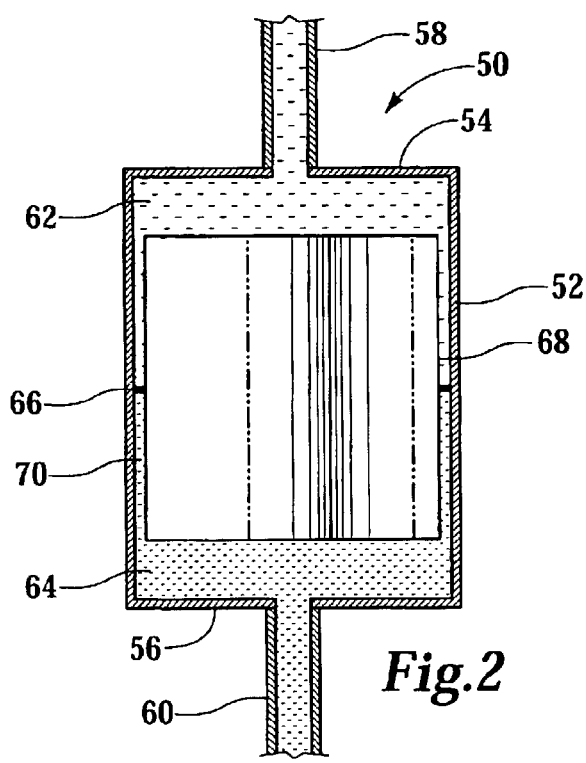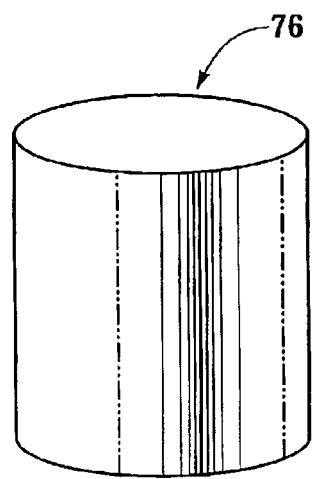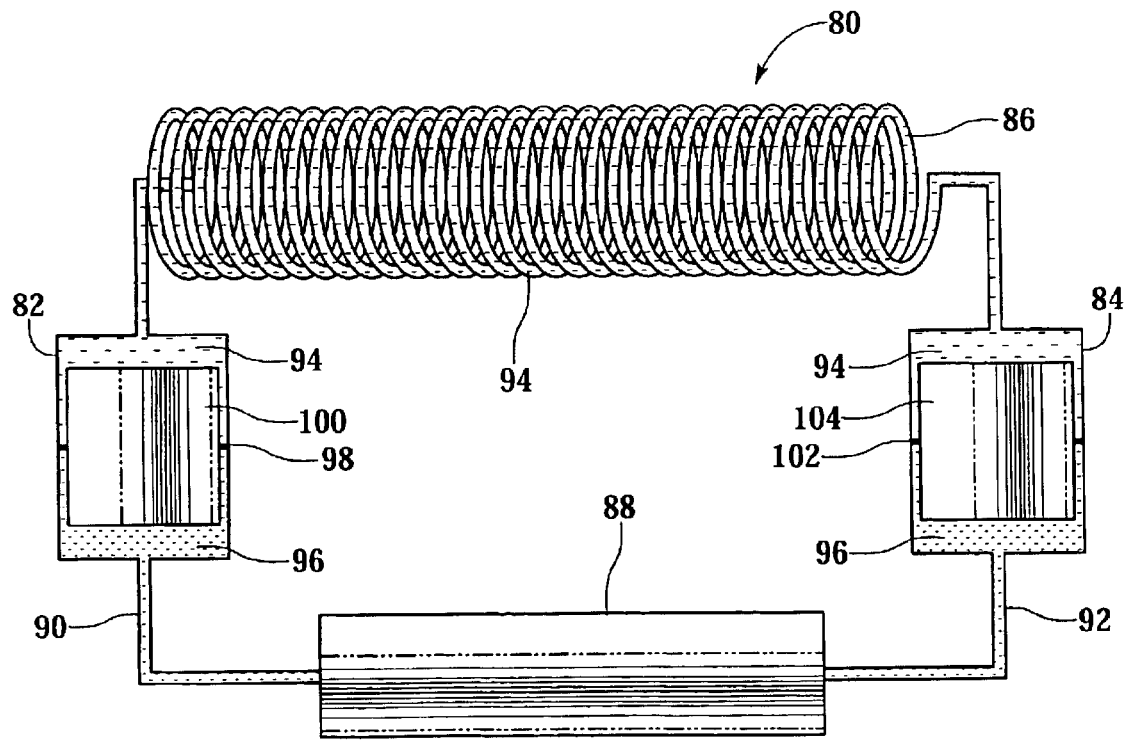
Fig.2
Fig.3
Fig.4

APPARATUS AND METHOD FOR MEASURING VISCOSITY

TECHNICAL FIELD OF THE INVENTION

This invention relates in general to measuring the viscosity of a sample fluid and in particular to an apparatus and method for measuring the viscosity of a sample fluid by creating a pressure drop in a capillary tube by forcing the sample fluid therethrough.

BACKGROUND OF THE INVENTION

During the development and production of a hydrocarbon bearing formation, small quantities of well fluids, or sample fluids, are obtained for analysis. Specifically, a sample fluid is extracted from the formation and transferred to laboratory equipment so that physical properties of the sample fluid, such as specific gravity, viscosity and salt water content, for example, may be determined. Of the aforementioned physical properties, the viscosity of a sample fluid, i.e., the sample fluid's resistance to flow or the sample fluid's ratio of shear stress to shear rate, is of particular importance to the development and production of a hydrocarbon bearing formation.

Numerous techniques and pieces of laboratory equipment are available for measuring the viscosity of the sample fluid. Various factors that are considered when determining the appropriate technique and equipment for measuring viscosity include the potential viscosity of the sample fluid, the state of the sample fluid, conditions, i.e., temperature and pressure, at which the measurements are to be made, and the volume of the sample fluid available for the measurements.

A capillary tube viscometer provides a convenient and reliable method for measuring the viscosity for a wide range of sample fluids. In principal, the capillary tube viscometer is an instrument for measuring viscosity of a sample fluid by passing the sample fluid at a known flow rate through a capillary tube which has a known diameter and a known length.

Quite often, the most pressing limitation in determining the viscosity of a sample fluid is the volume of the sample size available. This is particularly true in instances of offshore exploration for hydrocarbons wherein a small volume, such as 20 mL, of the sample fluid is collected for testing. Many viscometers, however, may have a working volume requirement far in excess of 20 mL and often approaching 500 mL.

To overcome the working volume limitations, some existing viscometers utilize mercury as a weighted fluid. Mercury is an incompressible, non-corrosive, non-interacting, well-characterized liquid that can be used to fill the volumetric gap and exert hydraulic pressure on a sample fluid without in any way altering the properties of the sample. Specifically, mercury (Hg) is a silvery liquid metal that is stable with air and water and unreactive to acids, except concentrated nitric acid ($HNO_3$), and alkalis. In addition, mercury is stable across a wide range of temperatures, i.e., mercury is liquid at room temperature and has a melting point of 234.28 K and a boiling point of 629.73 K. The density of mercury is 13,546 $K/m^3$ at 293K which is far greater than the density of the formation sample fluids. The single most potent attribute of mercury is its non-interacting features, i.e., mercury left in contact indefinitely with an aqueous or hydrocarbon system will shown no interaction. Consequently, the properties of the aqueous or hydrocarbon systems do not change, and any measurements made on the fluid phase in contact with mercury can be safely assumed to represent the true properties of the fluid phase.

It has been found, however, that although mercury is a naturally occurring element that is present throughout the environment, human activity can release mercury into the environment that results in population poisonings, high-level exposures of occupational groups and contamination of aquatic-based food chains. In particular, when mercury enters water, biological processes transform it into a highly toxic form, such as methylmercury ($CH_3Hg$), that accumulates in fish and animals that each fish. Human exposure then results by eating the mercury-contaminated fish and animals. Accordingly, in order to protect people's health and the integrity of the environment, in recent years industries have been working to reduce the amount of mercury in the environment by searching for alternative processes and techniques which reduce the likelihood of mercury contamination or avoid the use of mercury.

Therefore, a need has arisen for an apparatus and method for measuring the viscosity of small volume sample fluids that closes the volumetric gap between the sample fluid and the working volume. In addition, a need has arisen for such an apparatus and method that preserve the integrity of the sample fluid. Further, a need has arisen for such an apparatus and method that eliminates the use of mercury.

SUMMARY OF THE INVENTION

The present invention disclosed herein provides an apparatus and method for measuring viscosity. The present invention closes the volumetric gap between the sample fluid and the working volume of the viscometer so that the viscosity of small aliquots of sample fluids may be determined. Further, the present invention preserves the integrity of the sample fluid and eliminates the use of mercury. The present invention achieves these benefits by employing a holding vessel to receive a weighted fluid and the sample fluid. A floating spacer is buoyantly disposed in the weighted fluid and defines a narrow annular interface between the sample fluid and the weighted fluid in order to minimize mass transfer between the weighted fluid and the sample fluid during the testing process.

In one aspect, the present invention is directed to an apparatus for measuring the viscosity of a sample fluid that comprises a holding vessel that receives the sample fluid and a weighted fluid. The weighted fluid has a greater specific gravity than the sample fluid. A floating spacer is buoyantly disposed in the weighted fluid such that an interface between the sample fluid and the weighted fluid is defined between the holding vessel and the floating spacer. A capillary tube is positioned in fluid communication with the holding vessel such that a pressure drop is created across the capillary tube when at least a portion of the sample fluid is forced therethrough.

In one embodiment, the weighted fluid is an interactive fluid with respect to the sample fluid. The weighted fluid may include a salt having a cation such as sodium, calcium, magnesium, or cesium, for example. The salt may include a corresponding anion such as chloride or bromide, for example. The sample fluid may include a Newtonian fluid such as hydrocarbons or water, for example. The sample fluid may be forced through the capillary tube at a fixed flow rate. The floating spacer may include a material, such as titanium, that is non-reactive and non-corrosive with respect to the sample fluid and the weighted fluid. Additionally, an oven may provide a thermostatic environment for the capillary tube, the holding vessel and the floating spacer.

In another aspect, the present invention is directed to a system for measuring viscosity of a sample fluid that comprises an oven that provides a thermostatic environment. A first holding vessel receives the sample fluid and a weighted fluid. The weighted fluid has a greater specific gravity than the sample fluid. A first floating spacer is buoyantly disposed in the weighted fluid such that an interface between the sample fluid and the weighted fluid is defined between the first holding vessel and the first floating spacer. A second holding vessel is operable to receive the sample fluid and the weighted fluid. A second floating spacer is buoyantly disposed in the weighted fluid such that an interface between the sample fluid and the weighted fluid is defined between the second holding vessel and the second floating spacer. A capillary tube is in fluid communication with the first and second holding vessels such that the sample fluid may flow therethrough. A pump is in fluid communication with the first and second holding vessels such that the pump forces the weighted fluid into and out of the first and second holding vessels, thereby forcing at least a portion of the sample fluid through the capillary tube and creating a pressure drop thereacross.

In a further aspect, the present invention is directed to a method for measuring the viscosity of a sample fluid including loading a weighted fluid and the sample fluid into a holding vessel that is in fluid communication with a capillary tube, buoyantly disposing a floating spacer in the weighted fluid such that an interface between the sample fluid and the weighted fluid is defined between the holding vessel and the floating spacer, forcing at least a portion of the sample fluid through the capillary tube, measuring the pressure drop across the capillary tube and determining the viscosity of the sample fluid.

In one embodiment, the method includes the utilization of Hagen-Poisueille's law to calculate the viscosity. Prior to testing a sample fluid, the system may be calibrated to determine the tube constant of the capillary tube by pumping calibration fluid having a known viscosity through the capillary tube at a known volumetric flow rate and measuring the pressure drop across the capillary tube.

In a further aspect, the present invention is directed to an apparatus for minimizing mass transfer between a first fluid and a second fluid wherein the second fluid has a greater specific gravity than the first fluid. A holding vessel receives a volume of the first fluid and a volume of the second fluid. A floating spacer is buoyantly disposed in the second fluid such that an interface between the first fluid and the second fluid is defined between the holding vessel and the floating spacer. In this arrangement, the floating spacer provides a close fitting relationship with the interior wall that defines a narrow annular interface for the fluids.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 2 depicts a cross-sectional view of a holding vessel utilized in determining the viscosity of the sample fluid in accordance with the present invention;

FIG. 3 depicts a perspective view of a floating spacer of the present invention;

FIG. 4 illustrates a schematic diagram of the system for determining the viscosity of the sample fluid of the present invention in a first operational mode;

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Figure 1:
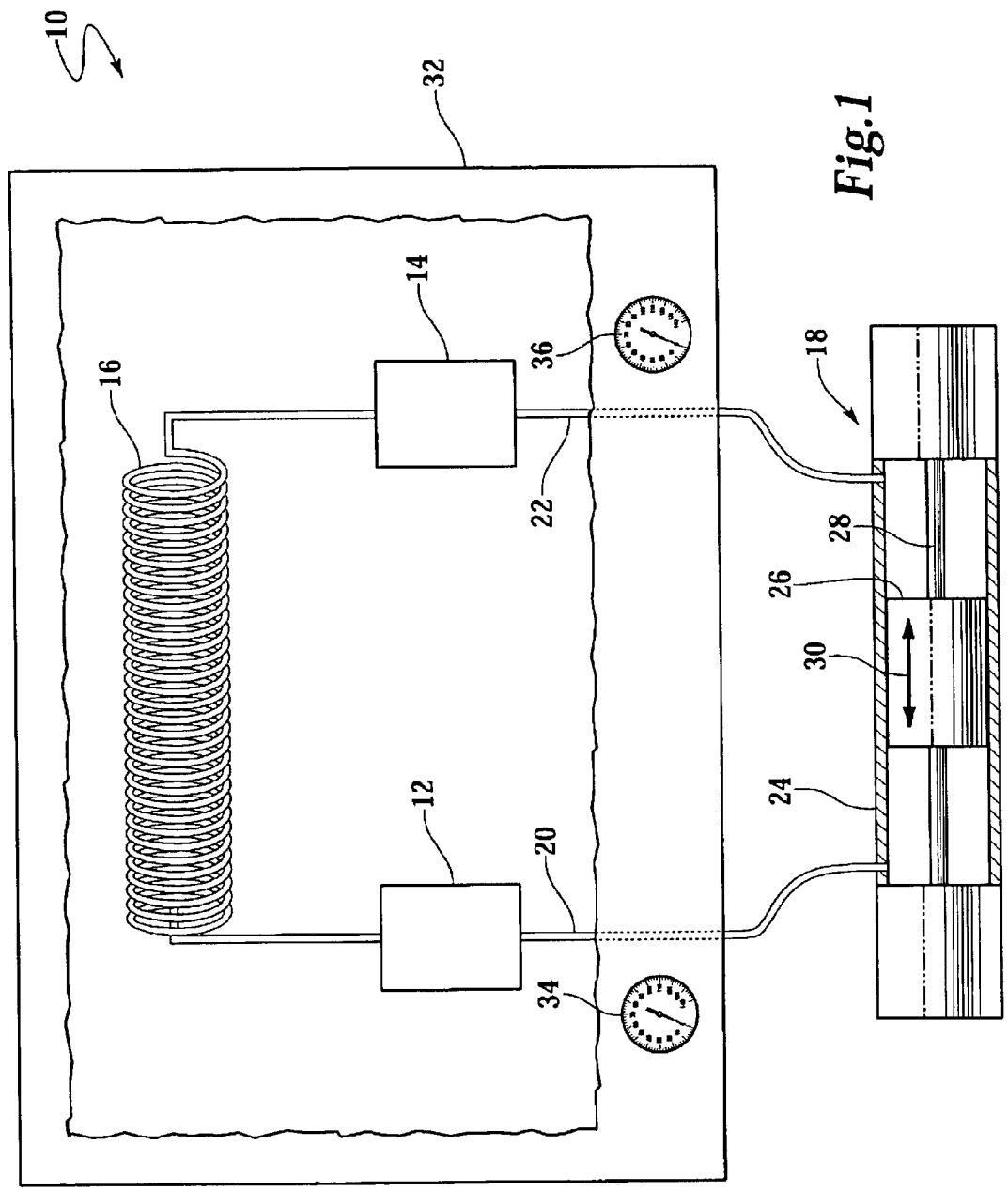
FIG. 1 depicts a plan view of a system for determining the viscosity of a sample fluid in accordance with the present invention.

Referring initially to FIG. 1, therein is depicted a system, which is generally designated 10, for determining the viscosity of a sample fluid in accordance with the present invention. Holding vessels 12, 14 are each in fluid communication with a capillary tube 16 which comprises a small diameter, cylindrical tube of a relatively large length. This construction maximizes the length to diameter ratio so that entrance and exit effects are minimized and a fully developed velocity profile is ensured. In particular, the diameter of the tube may in the range of 0.01 to 0.1 inches and the length of the tube may be up to or exceeding 50 feet. Depending on the experimental parameters such as potential pressure differential and potential viscosity, capillary tube 16 may be manufactured from Pyrex® glass or a metal alloy, for example.

A push-pull pump 18 is positioned in fluid communication with holding vessel 12 via tubing 20 and in fluid communication with holding vessel 14 via tubing 22. Push-pull pump 18 includes a housing 24 wherein a piston 26 comprising a metal cylinder is powered by a shaft 28 to reciprocate within housing 24 in either of two directions as illustrated by double-headed arrow 30. The reciprocation of piston 26 drives fluid into and out of holding vessels 12, 14. Specifically, when piston 26 is moving to the right in FIG. 1, fluid is being removed from holding vessel 12 and an equal amount of fluid is being pumped into holding vessel 14. Likewise, when piston 26 is moving the left in FIG. 1, fluid is being removed from holding vessel 14 and an equal amount of fluid is being pumped into holding vessel 12. As will be discussed in more detail hereinbelow, the reciprocating action of pump 18 and its associated fluid transfer, in turn, pushes a sample fluid through capillary tube 16 creating a pressure drop thereacross. The pressure drop is measured and used to determine the viscosity of the sample fluid according to Hagen-Poiseuille's Law. It should be appreciated by those skilled in the art that a variety of conventional electromechanical pumps may be employed in connection with system 10. For example, the pump may be a push-pull pump having two working pump sections, both of which are driven by a screw mechanism. In this embodiment, during normal working operation, one pump section would be pushing fluid out while the other pump section would be pulling in fluid. Since both pump elements are identically sized, both flow rates would be the same.

An oven 32 provides a heated enclosure for holding vessels 12, 14, capillary tube 16 and a portion of tubing 20, 22 in order to regulate the temperature during the viscosity determination. It should be appreciated by those skilled in the art that the thermostatic environment described herein may be provided by a different laboratory apparatus. For example, a thermostatic bath may provide the thermostatic environment. Pressure gauges 34, 36 are mounted at the base of oven 32 in order to display the aforementioned pressure drop measured across capillary tube 16.

FIG. 2 depicts a holding vessel 50 utilized in determining the viscosity of the sample fluid in accordance with the teachings of the present invention. Holding vessel 50 has a generally cylindrical shape defined by a side wall 52, a top wall 54 and a bottom wall 56. A fluid passageway 58 positioned at top wall 54 provides fluid communication with the capillary tube. Similarly, a fluid passageway 60 positioned at bottom surface 56 provides fluid communication with the push-pull pump.

A sample fluid 62 and a weighted fluid 64 are received by holding vessel 50. As depicted, sample fluid 62 has a lower specific gravity than weighted fluid 64 and is floating on top of weighted fluid 64. With this arrangement, sample fluid 62 and weighted fluid 64 form an interface 66 therebetween.

Sample fluid 62 may be a naturally occurring organic compound comprising hydrocarbons, water and other compounds. In one embodiment, sample fluid 62 may have been produced from a wellbore and have characteristics and a phase composition that are inexact or unknown at the time of testing. Preferably, the sample fluid 62 comprises a laminar, Newtonian fluid which is incompressible. Weighted fluid 64, which serves as a pressure transfer fluid, may be a water-based fluid having a greater density and therefore a greater specific gravity than sample fluid 62. In order that weighted fluid 64 has a greater specific gravity than sample fluid 62, a salt may be added to the water-based fluid. In one embodiment, a salt having a cation such as sodium, magnesium or cesium, for example, may be utilized. The corresponding anion of the salt may be chloride or bromide, for example. The salt weights up the water phase of weighted fluid 64 such that the density of weighted fluid 64 is suitable higher than the density of sample fluid 62. It should be appreciated that the precise composition of weighted fluid 64 including the selection and concentration of salt will depend on the density of sample fluid 62 as weighted fluid 64 is selected to be denser than sample fluid 62. It should be appreciated that although a particular sample fluid and weighted fluid have been described, the teachings of the present invention are applicable to any two fluids.

Mass transfer occurs between sample fluid 62 and weighted fluid 64 at interface 66 since sample fluid 62 and weighted fluid 64 are interactive fluids with respect to one another, i.e., sample fluid 62 and weighted fluid 64 have the capacity to combine with or diffuse into one another. According to the present invention, the interaction between weighted fluid 64 and sample fluid 62 is minimized by buoyantly disposing a floating spacer 68 in weighted fluid 64 such that interface 66 between sample fluid 62 and weighted fluid 64 is defined by annulus 70, i.e., the area between side wall 52 and floating spacer 68. Specifically, annulus 70 reduces the surface area of interface 66 between sample fluid 62 and weighted fluid 64. This arrangement offers a minimal cross-sectional area for mass transfer at interface 66 between sample fluid 62 and weighted fluid 64 and a very constricted passage alongside the height of floating spacer 68 for mass transfer between the fluids. Accordingly, floating spacer 68 minimizes the mass transfer or diffusion between sample fluid 62 and weighted fluid 64 by minimizing interface 66 between the two fluids in order to maintain the integrity of sample fluid 62. Preferably, the mass transfer between sample fluid 62 and weighted fluid 64 is no more than three percent over the course of the viscosity testing of sample fluid 62 which may be several hours to several days. More preferably, the mass transfer between sample fluid 62 and weighted fluid 64 is less than two percent over the course of the viscosity testing. Most preferably, the mass transfer between sample fluid 62 and weighted fluid 64 is less than one half of one percent over the course of the viscosity testing. Ideally, the mass transfer between sample fluid 62 and weighted fluid 64 is less than two tenth of one percent over the course of the viscosity testing.

Floating spacer 68 is selected for its close tolerances between the outside diameter of floating spacer 68 and the inside diameter of side wall 52. Floating spacer 68 does not contact side wall 52 or have any seal, such as an "O" ring seal, which bridges the gap between floating spacer 68 and side wall 52 since a seal would create resistance to movement and this resistance to movement would potentially influence the accuracy of the pressure measurements undertaken for the viscosity determination of sample fluid 62. Floating spacer 68 therefore provides hydraulic continuity between weighted fluid 64 and sample fluid 62. Hence, floating spacer 68 provides a minimal spacing between itself and side wall 52 of holding vessel 50 without forming a seal such that floating spacer 68 floats within holding vessel 50 without contacting side wall 52. This floating aspect is in addition to the buoyance floating spacer 68 exhibits with respect to weighted fluid 64 that insures that the interface between the two fluids stays intact at preferably approximately half way up the height of floating spacer 68.

FIG. 3 depicts a floating spacer 76 of the present invention. The shape of floating spacer 76 compliments the shape of the holding vessel into which floating spacer 76 will be placed such that a tight fitting relationship between the holding vessel and floating spacer 76 is present. In one embodiment, floating spacer 76 may be of a cylindrical shape and may be of either a solid construction or a hollow construction as long as the construction is able to withstand the high compressive loads due to the pressure requirements of the system while keeping the mass to a minimum. In some instances, the pressure requirements may be as high as 20,000 psi or higher. In particular, as previously discussed, the density, i.e., mass per unit volume, of floating spacer 76 must be optimized with respect to the weighted fluid such that floating spacer 76 floats in the weighted fluid. In one embodiment, the density of floating spacer 76 and density of the weighted fluid are optimized such that the interface meniscus between the sample fluid and the weighted fluid is approximately half way up the height of floating spacer 76. Preferably, floating spacer 76 comprises a material that is non-reactive and non-corrosive with respect to the sample fluid and the weighted fluid. In one embodiment, floating spacer 76 comprises titanium (Ti) which is generally non-reactive and very resistive to corrosion.

FIG. 4 illustrates a system for determining the viscosity of the sample fluid of the present invention in a first operational mode, which is generally designated by the numeral 80. First and second holding vessels 82, 84 are each in fluid communication with a capillary tube 86 and a pump 88. Tubing 90 provides the fluid communication between holding vessel 82 and pump 88 and tubing 92 provides the fluid communication between holding vessel 84 and pump 88. A sample fluid 94 is loaded into holding vessels 82, 84 and capillary tube 86 following the loading of a weighted fluid 96 into holding vessels 82, 84, tubing 90, 92 and pump 88. The amount of weighted fluid 96 loaded compensates for the volumetric gap between sample fluid 94 and the working volume of system 80. Weighted fluid 96 has a greater specific gravity than sample fluid 94, so sample fluid 94 floats on weighted fluid 96 and the two fluids form an interface 98. A floating spacer 100 is buoyantly disposed in weighted fluid 96 in holding vessel 82. Similarly, an interface 102 is defined between sample fluid 94 and weighted fluid 96 in holding vessel 84. A floating spacer 104 is buoyantly disposed in weighted fluid 96 in holding vessel 84.

In one embodiment, the following procedures may be employed to prepare the system for use. The system is evacuated by conventional practice, following which each of the two holding vessels 82, 84 is isolated. Using a separate pump for each holding vessel 82, 84, weighted fluid 96 is introduced into each holding vessel 82, 84 individually. With respect to holding vessel 82, as weighted fluid 96 is introduced into holding vessel 82, floating spacer 100, which is already positioned within holding vessel 82, can be expected to float, and will continue to do so until contact is made with the top of holding vessel 82 and floating spacer 100 can no longer move in the vertical direction. At this point all further injection of weighted fluid 96 ceases. As illustrated, the annular space between floating spacer 100 and holding vessel 82 is quite small, therefore any extra weighted fluid 96 injected into the system once floating spacer 100 tops out can be expected to quickly fill the annular space and overflow into the space above floating spacer 100. Experimentally, this is not desirable as the presence of weighted fluid 96 above floating spacer 100 can be expected to affect the properties of the sample to be studied. Consequently, caution must be exercised to ensure that there is minimal movement of weighted fluid 96 above the bottom level of floating spacer 100.

After holding vessel 82 has been properly filled, that side will be locked out, and holding vessel 84 may be similarly filled. Once floating spacer 104 is topped out in holding vessel 84, the sample fluid 96 can be loaded from the top of holding vessels 82, 84, one holding vessel at a time, to first occupy the minimal dead space above weighted fluid 96, and then the sample space above floating spacers 100, 104 as the sample charge is loaded. Once sample fluid 94 is loaded, viscosity determinations may commence.

Prior to performing a viscosity determination, however, the system may be calibrated with a calibration fluid of a known viscosity to determine a tube constant of the capillary tube. Specifically, the tube constant represents the radius or diameter of the capillary tube and the length of the capillary tube as these parameters are incorporated into Hagen-Poiseuille's equation, as explained below. The tube constant can be determined by pumping the calibration fluid through the capillary tube at a known volumetric flow rate and measuring the pressure drop across the capillary tube. Once calibration is complete and sample fluid 94 and weighted fluid 96 are properly loaded into the system, the viscosity of sample fluid 94 may be determined.

Figure 5:
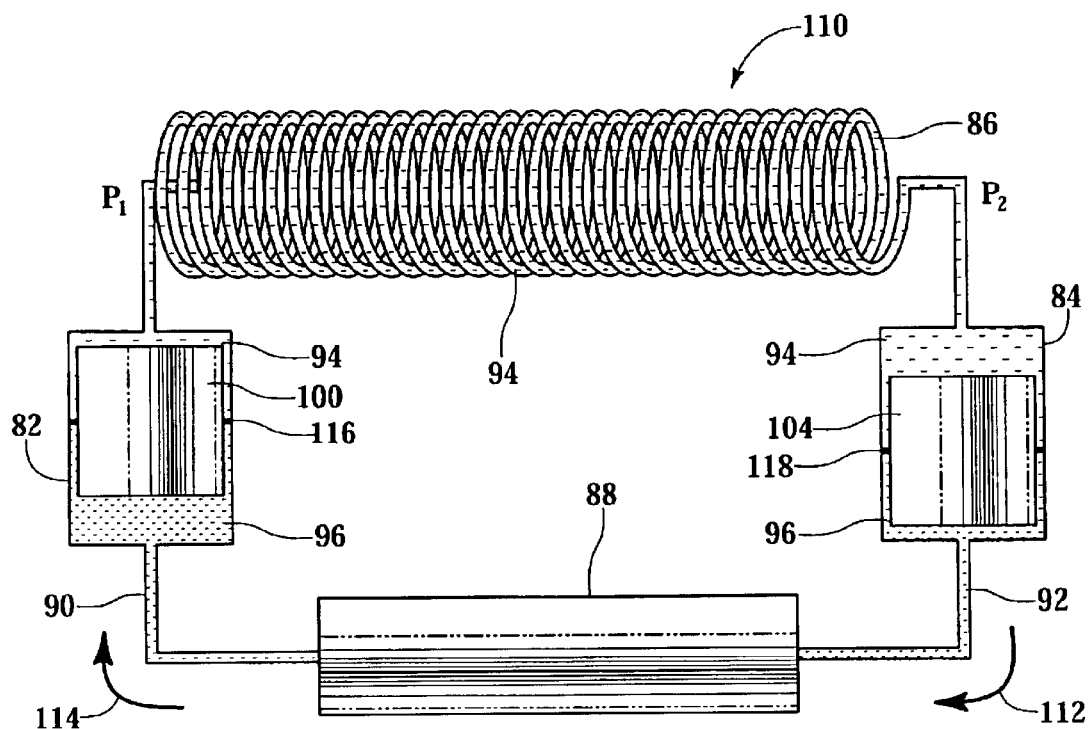
FIG. 5 illustrates a schematic diagram of the system for determining the viscosity of the sample fluid of the present invention in a second operational mode.

FIG. 5 illustrates the system for determining the viscosity of the sample fluid in a second operational mode, which is designated with numeral 110. Pump 88 forces weighted fluid 96 out of holding vessel 84 and into holding vessel 82 as indicated by arrows 112, 114. In particular, the rate at which fluid is forced out of holding vessel 84 is equal to the rate at which fluid is forced into holding vessel 86. The transfer of weighted fluid 96 forces at least a portion of sample fluid 94 from holding vessel 82 through capillary tube 86 and into holding vessel 84. The fluid transfer is evident by comparing interfaces 116, 118 with interfaces 98, 102 of FIG. 4. A pressure drop is associated with this fluid transfer across capillary tube 86 as indicated by the designations $P_1$ and $P_2$, such that the following relation holds:

$$\Delta P = P_1 - P_2$$

Once the pressure drop across the capillary tubes is measured, the viscosity $\mu$ of the sample fluid may be determined by utilizing Hagen-Poiseuille's law. Specifically, the instant pumping arrangement removes weighted fluid from one of the holding vessels and provides weighted fluid to the other holding vessel at an accurately calibrated predetermined rate Q. The effective radius r of the capillary passage and its length L are known or determined by conventional calibration practices. The differential pressure $\Delta P$ is the difference in the pressure across the capillary tube, as measured by pressure detectors and displayed on the aforementioned pressure gauges. This data is preferably supplied to a computer, which can automatically provide the viscosity $\mu$ of the fluid in terms of Hagen-Poiseuille's equation:

$$\mu = \frac{\pi \Delta P r^4}{8 L Q}$$

In standard notation, the viscosity $\mu$ is expressed in Poises, or dyne-seconds per square centimeter. The pressure head $\Delta P$ is expressed in dynes per square centimeter, the radius of the capillary tube r in centimeters, the length L in centimeters, and the rate of flow Q of fluid in cubic centimeters per second. It should be appreciated that the methodologies explained herein permit determination of any fluid viscosity at any Reynolds number value in the laminar flow range, with extension into the turbulent zone by applying the appropriate mathematical computations.

Figure 6:
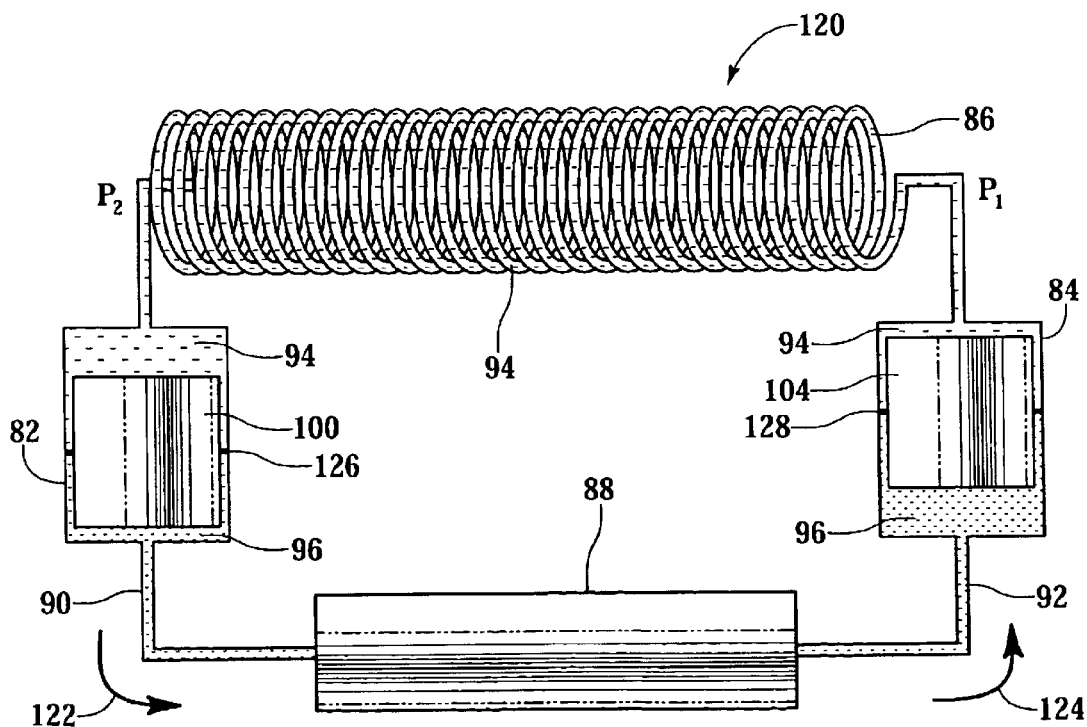
FIG. 6 illustrates a schematic diagram of the system for determining the viscosity of the sample fluid of the present invention in a third operational mode.

FIG. 6 illustrates the system for determining the viscosity of the sample fluid in a third operational mode, which is designated by the numeral 120. In instances where only a limited amount of sample is available, pump 88 moves the small amount of sample back and forth between holding vessels 82, 84 via capillary tube 86. As illustrated, pump 88 forces weighted fluid 96 out of holding vessel 86 and into holding vessel 84 at a constant rate as indicated by arrows 122, 124. The transfer of weighted fluid 96 forces at least a portion of sample fluid 94 from holding vessel 84 through capillary tube 86 and into holding vessel 82. The fluid transfer is evident by comparing interfaces 126, 128 with interfaces 98, 102 of FIG. 4 and interfaces 116, 118 of FIG. 5. The pressure drop $\Delta P$ associated with this fluid transfer across capillary tube 86 is indicated by the designations $P_1$ and $P_2$. This $\Delta P$ may be utilized to determine the viscosity p of sample fluid 86. In particular, pump 88 may continue to reciprocate as illustrated in FIGS. 5 and 6 so that many $\Delta P$ measurements may be performed and the viscosity of sample fluid 86 determined with a maximum signal-to-noise ratio and minimum error. Hence, the present invention provides an alternative to mercury that minimizes mass transfer between the sample fluid and the weighted fluid. In particular, the floating spacer of the present invention provides an extremely small cross-sectional surface area between the sample fluid and the weighted fluid that is positioned within the annulus between the floating spacer and the holding vessel such that an effective barrier is positioned that limits mass transfer between the fluids and maintains the integrity of the sample fluid during testing.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. An apparatus for measuring the viscosity of a sample fluid comprising:
   a holding vessel operable to receive the sample fluid and a weighted fluid, the weighted fluid having a greater specific gravity than the sample fluid;
   a floating spacer buoyantly disposed in the weighted fluid such that an interface between the sample fluid and the weighted fluid is defined between the holding vessel and the floating spacer; and
   a capillary tube in fluid communication with the holding vessel such that a pressure drop is created across the capillary tube when at least a portion of the sample fluid is forced therethrough.

2. The apparatus as recited in claim 1 wherein the weighted fluid further comprises a non-inert, interactive fluid with respect to the sample fluid.

3. The apparatus as recited in claim 1 wherein the sample fluid further comprises a Newtonian fluid.

4. The apparatus as recited in claim 1 wherein the sample fluid further comprises hydrocarbons.

5. The apparatus as recited in claim 1 wherein the weighted fluid further comprises water.

6. The apparatus as recited in claim 1 wherein the weighted fluid further comprises a salt having a cation selected from the group consisting of sodium, calcium, magnesium and cesium.

7. The apparatus as recited in claim 1 wherein the weighted fluid further comprises a salt having an anion selected from the group consisting of chloride and bromide.

8. The apparatus as recited in claim 1 wherein the sample fluid is forced through the capillary tube at a fixed flow rate.

9. The apparatus as recited in claim 1 wherein the floating spacer further comprises a material that is non-reactive and non-corrosive with respect to the sample fluid and the weighted fluid.

10. The apparatus as recited in claim 1 wherein the floating spacer further comprises titanium.

11. The apparatus as recited in claim 1 further comprising an oven which provides a thermostatic environment, wherein the capillary tube and holding vessel are positioned within the oven.

12. A system for measuring the viscosity of a sample fluid comprising:
    an oven operable to provide a thermostatic environment;
    a first holding vessel operable to receive the sample fluid and a weighted fluid, the weighted fluid having a greater specific gravity than the sample fluid;
    a first floating spacer buoyantly disposed in the weighted fluid such that an interface between the sample fluid and the weighted fluid is defined between the first holding vessel and the first floating spacer;
    a second holding vessel operable to receive the sample fluid and the weighted fluid;
    a second floating spacer buoyantly disposed in the weighted fluid such that an interface between the sample fluid and the weighted fluid is defined between the second holding vessel and the second floating spacer;
    a capillary tube in fluid communication with the first and second holding vessels; and
    a pump in fluid communication with the first and second holding vessels such that the pump forces the weighted fluid into and out of the first and second holding vessels, thereby forcing at least a portion of the sample fluid through the capillary tube and creating a pressure drop thereacross.

13. The apparatus as recited in claim 12 wherein the weighted fluid further comprises a non-inert, interactive fluid with respect to the sample fluid.

14. The apparatus as recited in claim 12 wherein the sample fluid further comprises a Newtonian fluid.

15. The apparatus as recited in claim 12 wherein the sample fluid further comprises hydrocarbons.

16. The apparatus as recited in claim 12 wherein the weighted fluid further comprises water.

17. The apparatus as recited in claim 12 wherein the weighted fluid further comprises a salt having a cation selected from the group consisting of sodium, calcium, magnesium and cesium.

18. The apparatus as recited in claim 12 wherein the weighted fluid further comprises a salt having an anion selected from the group consisting of chloride and bromide.

19. The apparatus as recited in claim 12 wherein the pump forces the weighted fluid into and out of the first and second holding vessels at a fixed flow rate.

20. The apparatus as recited in claim 12 wherein the floating spacer further comprises a material that is non-reactive and non-corrosive with respect to the sample fluid and the weighted fluid.

21. The apparatus as recited in claim 12 wherein the floating spacer further comprises titanium.

22. A method for determining the viscosity of a sample fluid comprising the step of:
    loading a weighted fluid and the sample fluid into a holding vessel that is in fluid communication with a capillary tube, the weighted fluid having a greater specific gravity than the sample fluid;
    buoyantly disposing a floating spacer in the weighted fluid such that an interface between the sample fluid and the weighted fluid is defined between the holding vessel and the floating spacer;
    forcing at least a portion of the sample fluid through the capillary tube;
    measuring the pressure drop across the capillary tube; and
    determining the viscosity of the sample fluid.

23. The method as recited in claim 22 wherein determining the viscosity of the sample fluid further comprises utilizing Hagen-Poisueille's law to calculate the viscosity.

24. The method as recited in claim 22 wherein loading the sample fluid into the holding vessel further comprises loading between about 0.5 mL and 20 mL of the sample fluid into the holding vessel.

25. The method as recited in claim 22 further comprising performing a calibration by determining a tube constant of the capillary tube.

26. The method as recited in claim 22 further comprising maintaining the capillary tube and the holding vessel in a thermostatic environment.

27. The method as recited in claim 22 further comprising maintaining the mass transfer between the weighted fluid and the sample fluid to no more than three percent.

28. The method as recited in claim 22 further comprising maintaining the mass transfer between the weighted fluid and the sample fluid to less than two percent.

29. The method as recited in claim 22 further comprising maintaining the mass transfer between the weighted fluid and the sample fluid to less than one half of one percent.

30. The method as recited in claim 22 further comprising maintaining the mass transfer between the weighted fluid and the sample fluid to less than two tenths of one percent.

31. A method for determining the viscosity of a sample fluid comprising the step of:
loading a weighted fluid and the sample fluid into a holding vessel that is in fluid communication with a capillary tube, the weighted fluid having a greater specific gravity than the sample fluid and the weighted fluid being an interactive fluid with respect to the sample fluid;
forcing at least a portion of the sample fluid through the capillary tube;
measuring the pressure drop across the capillary tube;
maintaining the mass transfer between the weighted fluid and the sample fluid to no more than three percent; and
determining the viscosity of the sample fluid.

32. The method as recited in claim 31 wherein the step of maintaining the mass transfer between the weighted fluid and the sample fluid to no more than three percent further comprises maintaining the mass transfer between weighted fluid and the sample fluid to less than two percent.

33. The method as recited in claim 31 wherein the step of maintaining the mass transfer between the weighted fluid and the sample fluid to no more than three percent further comprises maintaining the mass transfer between weighted fluid and the sample fluid to less than one half of one percent.

34. The method as recited in claim 31 wherein the step of maintaining the mass transfer between the weighted fluid and the sample fluid to no more than three percent further comprises maintaining the mass transfer between weighted fluid and the sample fluid to less than two tenths of one percent.

35. The method as recited in claim 31 further comprising buoyantly disposing a floating spacer in the weighted fluid such that an interface between the sample fluid and the weighted fluid is defined between the holding vessel and the floating spacer.

36. The method as recited in claim 31 further comprising maintaining the capillary tube and the holding vessel in a thermostatic environment.

* * * * *